(12) United States Patent
Blades

(10) Patent No.: US 9,723,908 B1
(45) Date of Patent: Aug. 8, 2017

(54) EAR REPOISITIONING AND SHIELDING CLAMP

(71) Applicant: Nellie Blades, Inglewood, CA (US)

(72) Inventor: Nellie Blades, Inglewood, CA (US)

( * ) Notice: Subject to any disclaimer, the term of this patent is extended or adjusted under 35 U.S.C. 154(b) by 0 days.

(21) Appl. No.: 15/040,591

(22) Filed: Feb. 10, 2016

(51) Int. Cl.
*A42B 1/06* (2006.01)
*A45D 44/12* (2006.01)
*A61F 11/14* (2006.01)

(52) U.S. Cl.
CPC .............. *A45D 44/12* (2013.01); *A61F 11/14* (2013.01)

(58) Field of Classification Search
CPC .......... A45D 44/12; A45D 40/30; A45D 2/00; A45D 24/36; A45D 19/18; A41D 13/081; A61F 11/14; A42B 3/166
USPC .... 2/174, 208, 209, 423; 132/319, 212, 213, 132/270
See application file for complete search history.

(56) References Cited

U.S. PATENT DOCUMENTS

| | | | | |
|---|---|---|---|---|
| 428,511 | A * | 5/1890 | Moore | A61F 11/14 2/209 |
| 2,159,435 | A * | 5/1939 | Gribbin | A45D 44/12 132/212 |
| 2,712,134 | A * | 7/1955 | Cyr | A61F 11/06 2/209 |
| 3,354,471 | A * | 11/1967 | Longo | A61F 11/06 2/174 |
| 3,452,365 | A | 7/1969 | Wallace | |
| 5,615,417 | A * | 4/1997 | Jackson | A45D 44/12 2/209 |
| 6,505,633 | B2 | 1/2003 | Mosely | |
| 7,469,429 | B1 | 12/2008 | Lanclos | |
| 7,865,974 | B1 | 1/2011 | Heller | |
| D662,262 | S | 6/2012 | Jones | |
| 2002/0023285 | A1* | 2/2002 | Mosely | A45D 44/12 2/174 |
| 2012/0017359 | A1 | 1/2012 | Parris et al. | |

FOREIGN PATENT DOCUMENTS

WO    WO2013129965    9/2013

* cited by examiner

Primary Examiner — Tejash Patel

(57) ABSTRACT

An ear repositioning and shielding clamp for protecting an ear from heat sources used in hair styling includes a pinch handle that is spring loaded. Each of a pair of jaws has a first edge coupled to the pinch handle. The jaws are substantially rigid. The jaws are biased to a closed position when the pinch handle is not pinched. Each of a pair of pads is coupled to a respective jaw. The pinch handle is configured to be pinched by the user, such that the jaws move in opposition to an open configuration to position the jaws around the ear. The pinch handle, upon release by the user, will motivate the jaws to resume a substantially closed position, inducing the user's ear to a safer position. The pads are configured to protect the user's ear from a nearby source of heat.

14 Claims, 4 Drawing Sheets

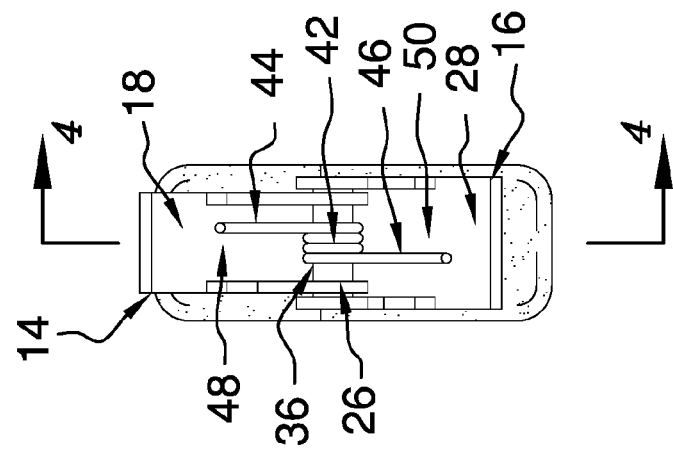
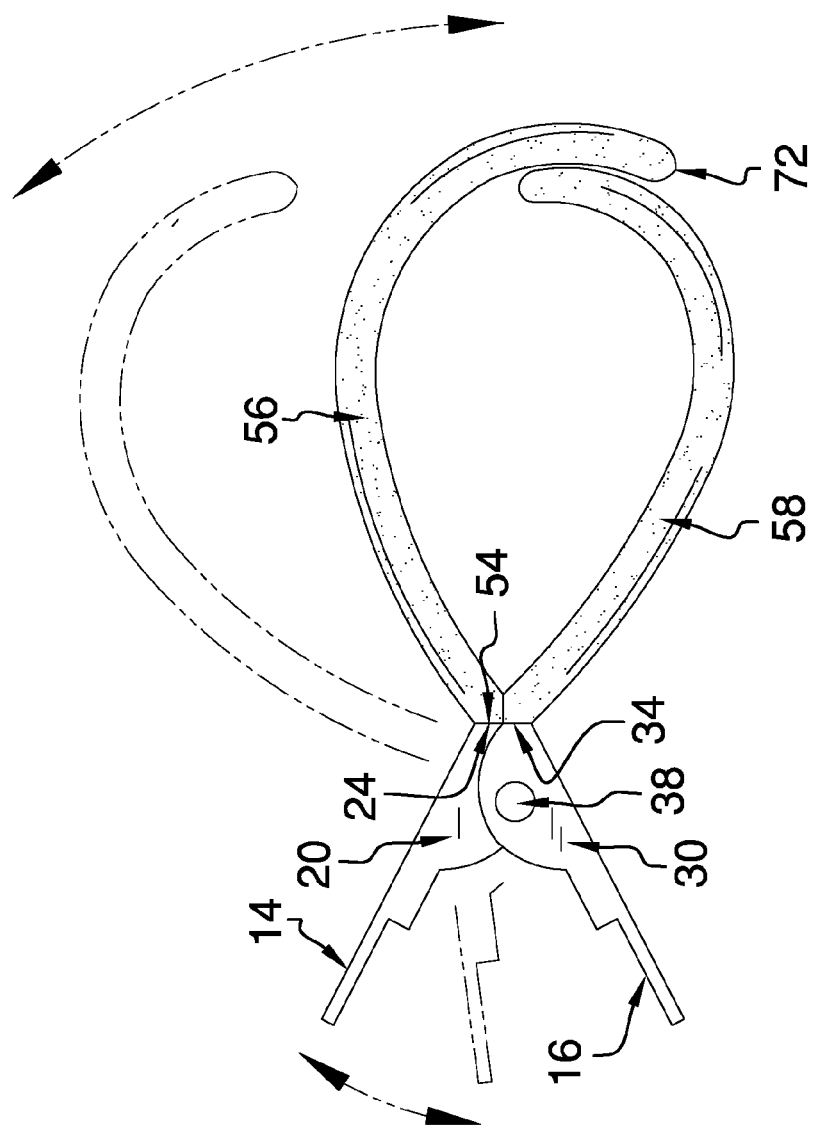
FIG. 3
FIG. 2

EAR REPOISITIONING AND SHIELDING CLAMP

BACKGROUND OF THE DISCLOSURE

Field of the Disclosure

The disclosure relates to clamps and more particularly pertains to a new clamp for protecting an ear from heat sources used in hair styling.

SUMMARY OF THE DISCLOSURE

An embodiment of the disclosure meets the needs presented above by generally comprising a pinch handle that is spring loaded. Each of a pair of jaws has a first edge coupled to the pinch handle. The jaws are substantially rigid. The jaws are biased to a closed position when the pinch handle is not pinched. Each of a pair of pads is coupled to a respective jaw. The pinch handle is configured to be pinched by the user, such that the jaws move in opposition to an open configuration to position the jaws around the ear. The pinch handle, upon release by the user, will motivate the jaws to resume a substantially closed position, inducing the user's ear to a safer position. The pads are configured to protect the user's ear from a nearby source of heat.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF THE DRAWINGS

The disclosure will be better understood and objects other than those set forth above will become apparent when consideration is given to the following detailed description thereof. Such description makes reference to the annexed drawings wherein:

FIG. 2 is a side view of an embodiment of the disclosure.

FIG. 3 is an end view of an embodiment of the disclosure.

DESCRIPTION OF THE PREFERRED EMBODIMENT

Figure 1:
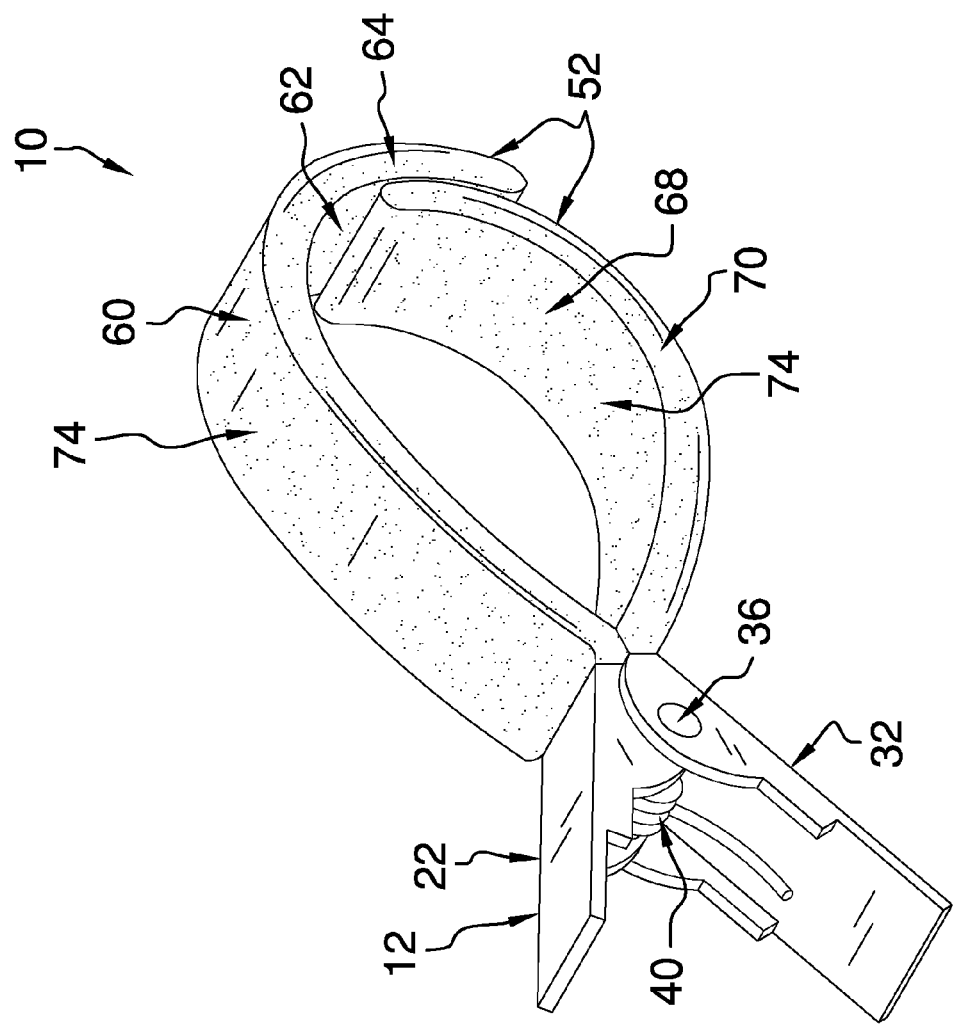
FIG. 1 is an isometric perspective view of an ear repositioning and shielding clamp according to an embodiment of the disclosure.
Figure 4:
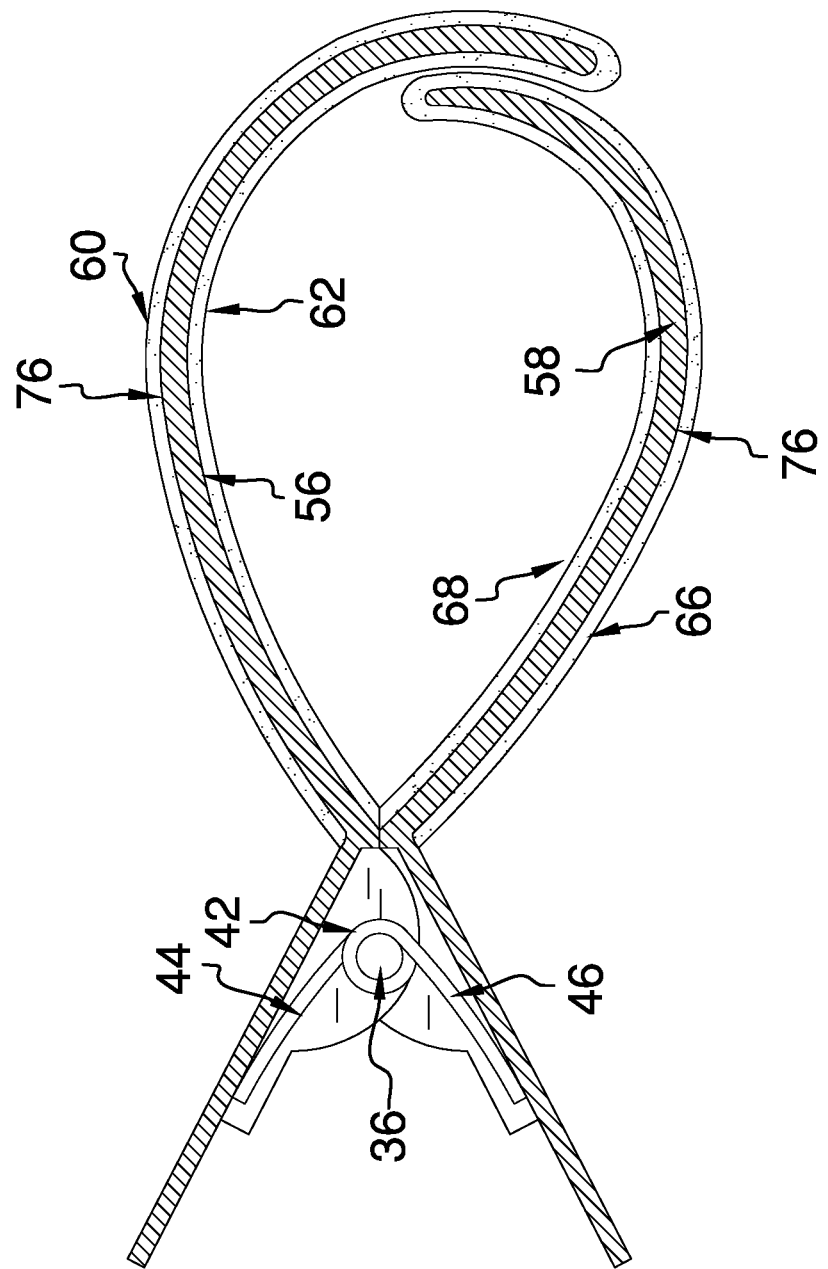
FIG. 4 is a cross-sectional view of an embodiment of the disclosure.
Figure 5:
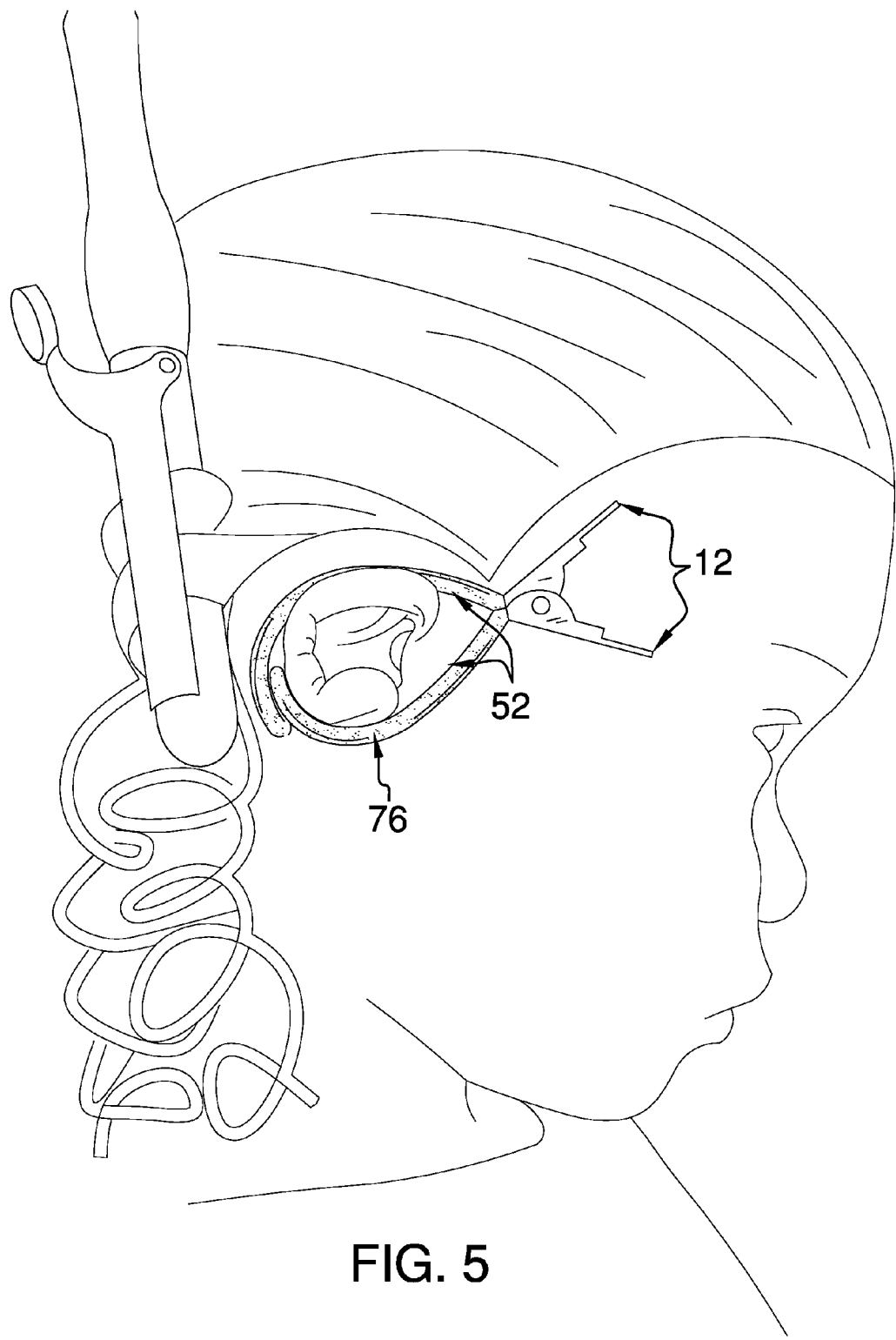
FIG. 5 is an in-use view of an embodiment of the disclosure.

With reference now to the drawings, and in particular to FIGS. 1 through 5 thereof, a new clamp embodying the principles and concepts of an embodiment of the disclosure and generally designated by the reference numeral 10 will be described.

As best illustrated in FIGS. 1 through 5, the ear repositioning and shielding clamp 10 generally comprises a pinch handle 12 that is spring loaded. More specifically, the pinch handle 12 comprises a movable handle 14 and a fixed handle 16. The movable handle 14 comprises a first plate 18 that is rigid and substantially rectangularly shaped. Each of a pair of first tabs 20 is coupled to and extends transversely from a respective opposing edge 22 of the movable handle 14. The first tabs 22 are positioned proximate to a first end 24 of the movable handle 14. The first tabs 22 are arcuate. Each of a pair of openings 26 is substantially centrally positioned through a respective first tab 22. The pair of openings 26 is aligned.

The fixed handle 16 comprises a second plate 28 that is rigid and substantially rectangularly shaped. The second plate 28 is dimensionally wider than the first plate 18. Each of a pair of second tabs 30 is coupled to and extends transversely from a respective opposing rim 32 of the fixed handle 16. The second tabs 32 are positioned proximate to a first terminus 34 of the fixed handle 16. The second tabs 32 are arcuate.

The pinch handle 12 also comprises a pivot pin 36 that is complementary to and positioned through the pair of openings 26. The pivot pin 36 has opposing ends 38. Each opposing end 38 is coupled to a respective second tab 30, such that the first plate 18 is pivotable relative to the second plate 28. A spring 40 that comprises a coiled section 42, a first extension 44 and a second extension 46 is positioned around the pivot pin 36. The first extension 44 is positioned adjacent to the movable handle 14. The first extension 44 extends from the coiled section 42 to proximate to a midpoint 48 of the first plate 18. The second extension 46 is positioned adjacent to the fixed handle 16. The second extension 46 extends from the coiled 42 section to proximate to a center 50 of the second plate 28. The coiled section 42 is positioned around the pivot pin 36 such that the first extension 44 engages the movable handle 14 and the second extension 46 engages the fixed handle 16. The movable handle 14 is biased in opposition to the fixed handle 16.

Each of a pair of jaws 52 has a first edge 54 that is coupled to the pinch handle 12. The jaws 52 are substantially rigid and arcuate. The pair of jaws 52 is biased to a closed position when the pinch handle 12 is not pinched. More specifically, the pair of jaws 52 comprises a movable jaw 56 and a fixed jaw 58. The movable jaw 56 is coupled to and extends transversely from the first end 24 the movable handle 14. The movable jaw 56 has a first exterior surface 60, a first interior surface 62, and a pair of first opposing sides 64.

The fixed jaw 58 is coupled to and extends transversely from the first terminus 34 of the fixed handle 16. The fixed jaw 58 has a second exterior surface 66, a second interior surface 68, and a pair of second opposing sides 70. Preferably, the movable jaw 56 is dimensionally longer than the fixed jaw 58, such that a second edge 72 of the movable jaw 56 overlaps the second exterior surface 66 of the fixed jaw 58 when the pinch handle 12 is not pinched. The first exterior surface 60, the second exterior surface 66, the first interior surface 62 and the second interior surface 68 are substantially semicirculary shaped. Each jaw 52 has a second edge 72 that is rounded.

Each of a pair of pads 74 is coupled to a respective jaw 52. Preferably, a respective pad 74 is coupled to the first exterior surface 60, the first interior surface 62, and the pair of first opposing sides 64 of the movable jaw 56. Also preferably, a respective pad 74 is coupled to the second exterior surface 66, the second interior surface 68, and the pair of second opposing sides 70. The pads 74 comprise a heat resistant material 76.

In use, the pinch handle is configured to be pinched by the user, inducing the pair of jaws to move in opposition to an open configuration. The pair of jaws in the open configuration is configured to position around an ear. The pinch handle, upon release by the user, will motivate the pair of jaws to resume a substantially closed position, inducing the user's ear to a safer position. The pair of pads is configured to protect the user's ear from a nearby source of heat.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:

1. An ear repositioning and shielding clamp comprising:
   a pinch handle, said pinch handle being spring loaded;
   a pair of jaws, each said jaw having a first edge coupled to said pinch handle, said jaws being substantially rigid, wherein said pair of jaws are biased to a closed position when said pinch handle is not pinched;
   a pair of pads, each said pad being coupled to a respective said jaw; and
   wherein said pinch handle is configured to be pinched by the user, such that said pair of jaws move in opposition to an open configuration, wherein said pair of jaws is configured to position around an ear, such that said pinch handle upon release by the user will motivate said pair of jaws to resume a substantially closed position, inducing the user's ear to a safer position, and wherein said pair of pads are configured to protect the user's ear from a nearby source of heat, said pinch handle comprising
     a movable handle, said movable handle comprising a first plate, said first plate being rigid,
     a pair of first tabs, each said first tab being coupled to and extending transversely from a respective opposing edge of said movable handle,
     a pair of openings, each said opening being substantially centrally positioned through a respective said first tab, said pair of openings being aligned,
     a fixed handle, said fixed handle comprising a second plate, said second plate being rigid, said second plate being dimensionally wider than said first plate,
     a pair of second tabs, each said second tab being coupled to and extending transversely from a respective opposing rim of said fixed handle,
     a pivot pin, said pivot pin being complementary to and positioned through said pair of openings, said pivot pin having opposing ends, each said opposing end being coupled to a respective said second tab, such that said first plate is pivotable relative to said second plate,
     a spring, said spring comprising a coiled section, said spring having a first extension and a second extension, said coiled section being positioned around said pivot pin, said first extension being positioned adjacent to said movable handle, said second extension being positioned adjacent to said fixed handle, and
     wherein said coiled section of said spring is positioned around said pivot pin such that said first extension engages said movable handle and such that said second extension engages said fixed handle, wherein said movable handle is biased in opposition to said fixed handle.

2. The clamp of claim 1, further including said jaws being arcuate.

3. The clamp of claim 1, further including said first plate and said second plate being substantially rectangularly shaped.

4. The clamp of claim 1, further comprising:
   said first tabs being positioned proximate to a first end of said movable handle; and
   said second tabs being positioned proximate to a first terminus of said fixed handle.

5. The clamp of claim 1, further including said first tabs and said second tabs being arcuate.

6. The clamp of claim 1, further comprising:
   said first extension extending from said coiled section to proximate to a midpoint of said first plate; and
   said second extension extending from said coiled section to proximate to a center of said second plate.

7. The clamp of claim 1, further including said pair of jaws comprising:
   a movable jaw, said movable jaw being coupled to and extending transversely from said first end said movable handle;
   a fixed jaw, said fixed jaw being coupled to and extending transversely from said first terminus of said fixed handle.

8. The clamp of claim 7, further comprising:
   said movable jaw having a first exterior surface, a first interior surface, and a pair of first opposing sides; and
   said fixed jaw having a second exterior surface, a second interior surface, and a pair of second opposing sides.

9. The clamp of claim 7, further including said movable jaw being dimensionally longer than said fixed jaw, such that a second edge of said movable jaw overlaps said second exterior surface of said fixed jaw when said pinch handle is not pinched.

10. The clamp of claim 8, further including said first exterior surface, said second exterior surface, said first interior surface and said second interior surface being substantially semicirculary shaped.

11. The clamp of claim 1, further including each said jaw having a second edge, said second edge being rounded.

12. The clamp of claim 8, further comprising:
    a respective said pad being coupled to said first exterior surface, said first interior surface, and said pair of first opposing sides of said movable jaw; and
    a respective said pad being coupled to said second exterior surface, said second interior surface, and said pair of second opposing sides.

13. The clamp of claim 1, further including said pair of pads comprising a heat resistant material.

14. An ear repositioning and shielding clamp comprising:
    a pinch handle, said pinch handle being spring loaded, said pinch handle comprising:

a movable handle, said movable handle comprising a first plate, said first plate being rigid, said first plate being substantially rectangularly shaped, a pair of first tabs, each said first tab being coupled to and extending transversely from a respective opposing edge of said movable handle, said first tabs being positioned proximate to a first end of said movable handle, said first tabs being arcuate, a pair of openings, each said opening being substantially centrally positioned through a respective said first tab, said pair of openings being aligned, a fixed handle, said fixed handle comprising a second plate, said second plate being rigid, second plate being substantially rectangularly shaped, said second plate being dimensionally wider than said first plate, a pair of second tabs, each said second tab being coupled to and extending transversely from a respective opposing rim of said fixed handle, said second tabs being positioned proximate to a first terminus of said fixed handle, said second tabs being arcuate, a pivot pin, said pivot pin being complementary to and positioned through said pair of openings, said pivot pin having opposing ends, each said opposing end being coupled to a respective said second tab, such that said first plate is pivotable relative to said second plate, a spring, said spring comprising a coiled section, said spring having a first extension and a second extension, said coiled section being positioned around said pivot pin, said first extension being positioned adjacent to said movable handle, said first extension extending from said coiled section to proximate to a midpoint of said first plate, said second extension being positioned adjacent to said fixed handle, said second extension extending from said coiled section to proximate to a center of said second plate, and wherein said coiled section of said spring is positioned around said pivot pin such that said first extension engages said movable handle and such that said second extension engages said fixed handle, wherein said movable handle is biased in opposition to said fixed handle;

a pair of jaws, each said jaw having a first edge coupled to said pinch handle, said jaws being substantially rigid, said jaws being arcuate, wherein said pair of jaws are biased to a closed position when said pinch handle is not pinched, said pair of jaws comprising:

a movable jaw, said movable jaw being coupled to and extending transversely from said first end said movable handle, said movable jaw having a first exterior surface, a first interior surface, and a pair of first opposing sides, a fixed jaw, said fixed jaw being coupled to and extending transversely from said first terminus of said fixed handle, said fixed jaw having a second exterior surface, a second interior surface, and a pair of second opposing sides, said movable jaw being dimensionally longer than said fixed jaw, such that a second edge of said movable jaw overlaps said second exterior surface of said fixed jaw when said pinch handle is not pinched, said first exterior surface, said second exterior surface, said first interior surface and said second interior surface being substantially semicirculary shaped;

each said jaw having a second edge, said second edge being rounded;

a pair of pads, each said pad being coupled to a respective said jaw, a respective said pad being coupled to said first exterior surface, said first interior surface, and said pair of first opposing sides of said movable jaw, a respective said pad being coupled to said second exterior surface, said second interior surface, and said pair of second opposing sides, said pair of pads comprising a heat resistant material; and wherein said pinch handle is configured to be pinched by the user, such that said pair of jaws move in opposition to an open configuration, wherein said pair of jaws is configured to position around an ear, such that said pinch handle upon release by the user will motivate said pair of jaws to resume a substantially closed position, inducing the user's ear to a safer position, and wherein said pair of pads are configured to protect the user's ear from a nearby source of heat.

* * * * *